US005547838A

United States Patent [19]
Nisson et al.

[11] Patent Number: 5,547,838
[45] Date of Patent: Aug. 20, 1996

[54] METHOD FOR THE RAPID AND ULTRA-SENSITIVE DETECTION OF LEUKEMIC CELLS

[75] Inventors: Paul E. Nisson; Nicoletta Sacchi, both of Gaithersburg, Md.

[73] Assignee: Life Technologies, Inc., Gaithersburg, Md.

[21] Appl. No.: 230,002

[22] Filed: Apr. 19, 1994

Related U.S. Application Data

[63] Continuation of Ser. No. 954,110, Oct. 1, 1992, abandoned.
[51] Int. Cl.⁶ .............................. C12Q 1/68; C12P 19/34; C07H 21/00
[52] U.S. Cl. ........................ 435/6; 435/91.2; 435/91.51; 536/24.31
[58] Field of Search .......................... 435/6, 91.2, 91.51; 536/24.31

[56] References Cited

U.S. PATENT DOCUMENTS 5,057,410  10/1991  Kawasaki et al. ........................ 435/6

OTHER PUBLICATIONS

Popp, S., et al. Translocation (8;21) in acute nonlymphocytic leukemia delineated by chromosomal in situ . . . Cancer Genet.Cytogenet.(Nov. 1991) 57:103–107.
Rabbitts, T., " Translocations, Master Genes, and Acute Differences between the Origins of Acute and Chronic Leukemias," *Cell* 67:641–644 (1991).
Cleary, M. L., "Oncogenic Conversion of Transcription Factors by Chromosomal Translocations", *Cell* 66:619–622 (1991).
Sawyers, C. L. et al., "Leukemia and the Disruption of Normal Hematopoieses," *Cell* 64:337–350 (1991).
Borrow, J. et al., " Moleacular Analysis of Acute Promyelocytic Leukemia Breakpoint Cluster Region on Chromosome 17," *Science* 249:1577–1580 (1990).

de Thé, H. et al. "The t(15;17) Translocation of Acute Promyelocytic Leukaemia Fuses the Retinoic Acid Receptor α Gene to a Novel Transcribed Locus," *Nature* 347:558–561 (1990).
Alcalay, M. et al., "Translocation Breakpoint of Acute Promyelocytic Leukemia within the Retinoic Acid Receptor α Locus," *Proc. Natl. Acad. Sci. (U.S.A.)* 88:1977–1981 (1991).
von Lindern, M. et al., "The (6;9) Chromosome Translocation, Associated with a Specific Subtype of Acute Nonlymphocytic Leukemia, Leads to Aberrant Transcription of a Target Gene on 9q34," *Molec. Cell. Biol.* 10:4016–4026 (1990).
Solomon, E. et al., "Chromosome Aberrations and Cancer," *Science* 254:1153–1160 (1991).
Miyoshi, H. et al., "t(8;21) Breakpoints on Chromosome 21 in Myeloid Leukemia Are Clustered within a Limited Region of a Single Gene, AML1," *Proc. Natl. Acad. Sci. (U.S.A.)* 88:10431–10434 (1991).
Erickson, P. et al., "Identification of Breakpoints in t(8;21) Acute Myelogenous Leukemia and Isolation of a Fusion Transcript, AML1/ETO, With Simlarity to Drosophila Segmentation Gene, *runt*," *Blood* 80:1825–1831 (1992).
Gao, J. et al., "Isolation of a Yeast Artificial Chromosome Spanning the 8;21 Translocation Breakpoint t(8;21)(q22;q22.3) in Myelogenous Leukemia," *Proc. Natl. Acad. Sci.(U.S.A.)* 88:4882–4886 (1991).
Kearney, L. et al., "DNA Sequences of Chromosome 21–Specific YAC Detect the t(8;21) Breakpoint of Acute Myelogenous Leukemia," *Cancer Genet. Cytogenet.* 57:109–119 (1991).

(List continued on next page.)

*Primary Examiner*—W. Gary Jones
*Assistant Examiner*—David Schreiber
*Attorney, Agent, or Firm*—Howrey & Simon; Jeffrey I. Auerbach

[57] ABSTRACT

An improved method is disclosed for diagnosing the presence of a chromosomal translocation characteristic of acute myelogenous leukemia. Nucleic acid molecules that may be used in this improved method are described.

3 Claims, 3 Drawing Sheets

OTHER PUBLICATIONS

Daga, A. et al., "Leukaemia/*Drosophila* Homology," *Nature* 356:484 (1992).

Xiong, Y. et al., "Molecular Cloning and Chromosomal Mapping of CCND Genes Encoding Human D-Type Cyclins," *Genomics* 13:575–584 (1992).

Xiong, Y. et al., "Human D-Type Cyclin," *Cell* 65:691–699 (1991).

Hunter, T. et al., "Cyclins and Cancer," *Cell* 66:1071–1074 (1991).

Motokura, T. et al., "A Novel Cyclin encoded by a *bcl1*-Linked Candidate Oncogene," *Nature* 350:512–515 (1991).

Withers, D. A. et al., "Characterization of a Candidate *bcl–1* Gene," *Molec. Cell. Biol.* 11:4846–4853 (1991).

Chomczynski, P. et al., "Single–Step Method of RNA Isolation by Acid Guanidinium Thiocyanate–Phenol–Chloroform Extraction," *Anal. Biochem.* 162:156–159 (1987).

```
ATCGTACTGAGAAGCACTCCACAATGCCAGACTCACCTGTGGATGTGAAG    50

ACGCAATCTAGGCTGACTCCTCCAACAATGCCACCTCCCCAACTACTCA    100

AGGAGCTCCAAGAACCAGTTCATTTACACCGACAACGTGTAAGTAGTCAT    150
       |||||||||  ||  || ||||||||||||||||
       GACCCGCGGAGAAGCTGTGCATTTACACCGACAAC   human cyclin D2 region

TTCAGGCTTTTGAGTTTCAGTTTAAAGTTTAAATTAAAATTTTTTTCTGC    200

AAATGAAAAATCAAGGGAAATAAAAATTCAGCATCAATGTATTATGCAGAA  250

TGAACC  -256
```

METHOD FOR THE RAPID AND ULTRA-SENSITIVE DETECTION OF LEUKEMIC CELLS

This is a continuation of application Ser. No. 07/954,110 filed Oct. 1, 1992, now abandoned.

FIELD OF THE INVENTION

The invention relates to improved methods for diagnosing the presence or onset of acute myelogenous leukemia (AML) in an individual. The invention also pertains to nucleic acid probes that are capable of recognizing a chromosomal translocation that is characteristic of AML.

BACKGROUND OF THE INVENTION

Leukemia is a progressive, malignant disease of the blood-forming organs, characterized by the abnormal proliferation and development of leukocytes, and their precursors in the blood and bone marrow. The disease is classified clinically on the basis of (1) whether the condition is acute or chronic, (2) whether it involves myeloid (i.e. myelogenous), lymphoid (non-myelogenous) or monocytic cells, and (3) whether it is associated with an increase in the concentration of abnormal cells in the blood.

A characteristic of leukemia is the presence of specific chromosomal abnormalities which are considered to be involved in tumor development (Rabbitts, T., *Cell* 67:641–644 (1991); Cleary, M. L., *Cell* 66:619–622 (1991), both herein incorporated by reference). In acute leukemia, such chromosomal abnormalities frequently activate transcription factors. These factors are often important in differentiation. Thus, for example, the activation of the c-myc gene, is associated with T-cell acute leukemia.

The best studied leukemic translocation is that which results in the presence of the Philadelphia chromosome, and has been found to be indicative of chronic myelogenous leukemia. This translocation fuses the c-ABL gene with BCR, a transcription unit on chromosome 22. The chimeric protein that results has been found to have growth promoting tyrosine kinase activity (Sawyers, C. L. et al., *Cell* 64:337–350 (1991)). Other well characterized translocations include the translocation of chromosomes 15 and 17, and 6 and 9, that are characteristic of acute promyelocytic leukemia, and acute myeloid leukemia, respectively (Borrow, J. et al., *Science* 249:1577–1580 (1990); de Thé, H. et al., *Nature* 347:558–561 (1990); Alcalay, M. et al., *Proc. Natl. Acad. Sci.* (U.S.A.) 88:1977–1981 (1991); von Lindern, M. et al., *Molec. Cell, Biol.* 10:4016–4026 (1990)).

The M2 and M1 AML is presently diagnosed using cytogenetic methods, and in particular, through karyotypic analysis of the chromosome 8 - 21 translocation. In general, the method is time consuming, and thus delays a conclusive diagnosis. Moreover, due to the nature of karyotypic analysis, the method requires highly trained technicians. More significantly, since karyotypic analysis can be effectively done only on small numbers of cells (e.g. 20–50 cells), and leukemic cells are present at a low concentration (relative to non-leukemic cells), the method is generally incapable of detecting a leukemic condition that affects less than 2–5% of the cells analyzed. It thus has significant drawbacks for monitoring the results of chemotherapy or tumor proliferation. Thus, a more rapid method for identifying individuals having a chromosomal 8–21 translocation would be highly desired. The present invention provides such a method.

SUMMARY OF THE INVENTION

The present invention provides improved methods for diagnosing the presence or onset of acute myelogenous leukemia (AML) of M2 or M1 subtype in a patient. The invention also encompasses probes capable of identifying the chromosome 8 - chromosome 21 translocation that is a characteristic of this disease.

In detail, the invention provides a method for diagnosing the presence of a leukemic cell in a sample comprising the steps:

A) incubating the sample in the presence of at least one nucleic acid molecule that is capable of hybridizing to:
  (1) a nucleotide sequence found in chromosome 8 of a non-leukemic human cell or
  (2) a nucleotide sequence found in chromosome 21 of a non-leukemic human cell; and B) diagnosing the presence by determining whether the sample contains a nucleic acid molecule, or is capable of forming a single cDNA molecule, that is capable of hybridizing to both a nucleotide sequence found in chromosome 8 of a non-leukemic human cell and a nucleotide sequence found in chromosome 21 of a non-leukemic human cell.

The invention also concerns the embodiments wherein either a single or at least two nucleic acid molecules are employed in step A.

The invention concerns the embodiment wherein a single nucleic acid employed in step A, and that nucleic acid molecule is substantially incapable of stably hybridizing to either chromosome 8 or chromosome 21 of a non-leukemic cell, but is capable of stably hybridizing to a chromosome 8 -chromosome 21 fusion, or to a cDNA produced from the fusion.

The invention concerns the embodiment wherein at least two different detectably labelled nucleic acid molecules employed in step A, and wherein the determination is accomplished by in situ hybridization.

The invention also concerns the embodiment wherein the at least two different nucleic acid molecules are primers, and wherein the determination is accomplished by a primer-mediated amplification of a sequence corresponding to a chromosome 8 -chromosome 21 fusion, or to a sequence corresponding to a cDNA produced from the fusion.

The invention also provides a composition of matter comprising:

(1) a nucleic acid molecule having a nucleotide sequence found in chromosome 8 of a non-leukemic human cell and (2) a nucleic acid molecule having a nucleotide sequence found in chromosome 21 of a non-leukemic human cell;

wherein the nucleic acid molecules are capable of hybridizing to a chromosome at respective sites that flank a chromosome 8 - chromosome 21 translocation characteristic of acute myelogenous leukemia.

The invention also concerns the embodiments wherein at least one of the nucleotide sequences is hybridized to its respective site and/or wherein at least one of the nucleic acid molecules is detectably labelled.

The invention particularly concerns the embodiments wherein at least one of the different nucleic acid molecules is selected from the group consisting of SEQ ID NOS: 1 and 2.

BRIEF DESCRIPTION OF THE FIGURES

FIG. 3 shows the sequence of the 3' region of the fusion transcript found in t(8;21) cells, that is derived from chromosome 8. Comparison of the 256 nucleotides against nucleotide sequences in the database revealed a region of nearly identical homology with a region of the human cyclin D2 gene (SEQ ID NO:17; SEQ ID NO:18).

DESCRIPTION OF THE PREFERRED EMBODIMENTS

Figure 1:
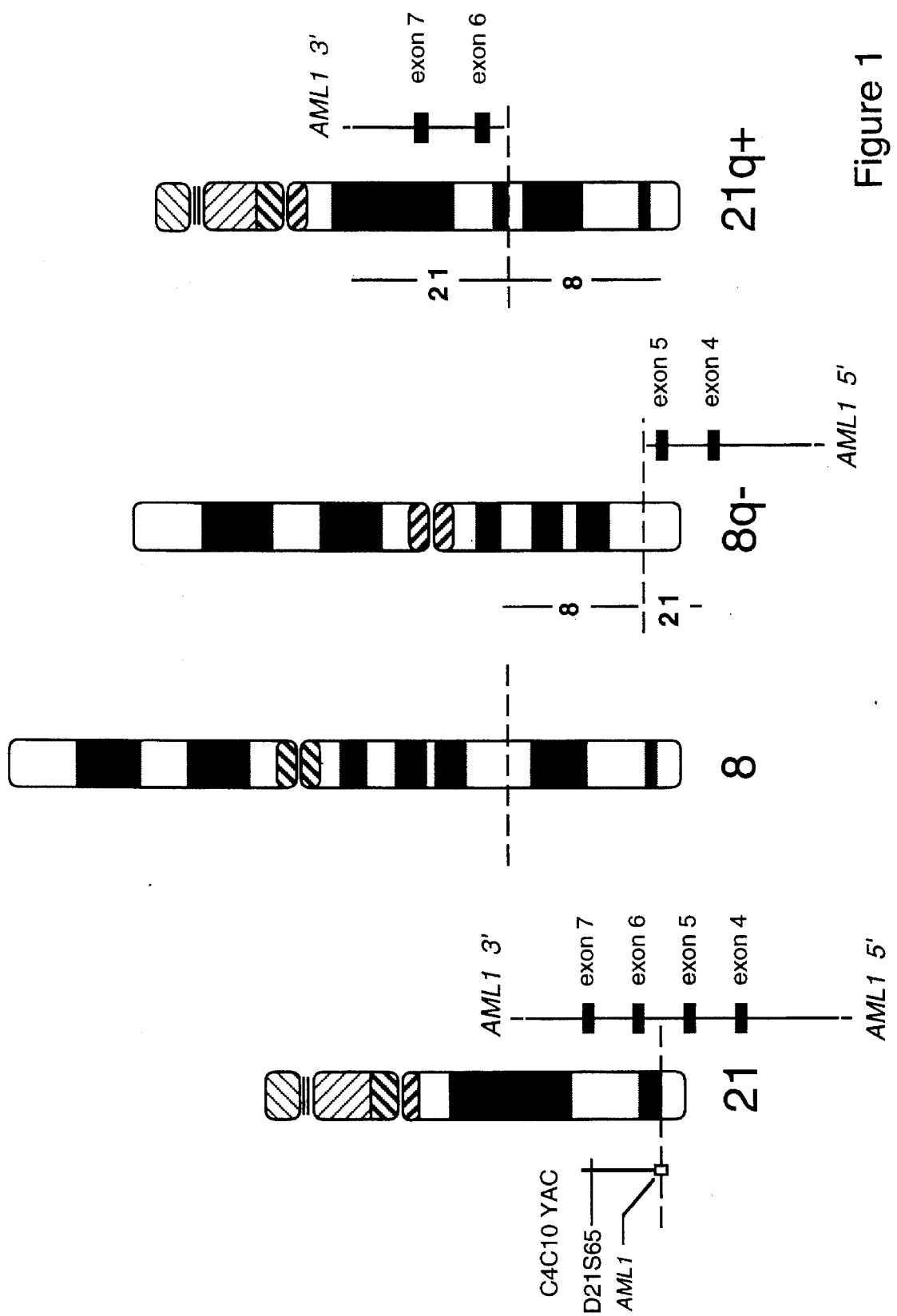
FIG. 1 shows an ideogram of the t(8;21)(q22;q22). The orientation of the AML1 gene is shown on normal chromosome 21 and the derivative chromosomes. The 3' centromeric region of the AML1 gene is contained in a YAC (C4C10), distal to the D21S65 locus. The breakpoint, denoted by the dotted line, occurs between AML1 exons 5 and 6.

The present invention provides a rapid, and highly sensitive assay that is capable of identifying a translocation between chromosome 8 and chromosome 21 indicative of AML M2 or M1 subtypes.

As used herein, the term "translocation" denotes the physical relocation of a segment of one chromosome to a position on a different chromosome, or to an abnormal position on its original chromosome. The occurrence of a translocation between chromosomes 8 and 21 is designated as "t(8;21)." The present invention derives, in part from the clonal isolation and sequencing of the "breakpoint" region that is formed through the translocation of chromosomes 8 and 21.

The invention identifies this translocation by analyzing the nucleic acid molecules (DNA—including cDNA—or RNA) of a sample for molecular species that are capable of hybridizing to nucleic acid molecules that are capable of hybridizing to sites that flank the breakpoint of the translocation (i.e. the point of chromosomal fusion between the chromosomes of the translocation).

Any sample capable of containing DNA or RNA of a cell may be exploited in accordance of the present invention. Thus, the sample may be tissue biopsies, cell preparations, cellular extracts, cDNA preparations, nucleic acid preparations, etc.

Since the breakpoint is a characteristic of a leukemic cell (i.e. a cell that is associated with the onset of or predisposition to leukemia), the detection of the breakpoint provides a means for diagnosing leukemia. Although the invention has several embodiments, the determination of the presence of a breakpoint is preferably accomplished through the use of nucleic acid hybridization.

As used herein, two sequences are said to be able to hybridize to one another if they are capable of forming an anti-parallel double-stranded nucleic acid structure. Conditions of nucleic acid hybridization suitable for forming such double stranded structures are described by Maniatis, T., et al. (In: *Molecular Cloning, A Laboratory Manual*, Cold Spring Harbor Laboratories, Cold Spring Harbor, N.Y. (1982)), and by Haymes, B. D., et al. (In: *Nucleic Acid Hybridization, A Practical Approach*, IRL Press, Washington, D.C. (1985)). Two sequence are said to be incapable of "stably hybridizing" to one another if they are incapable of remaining hybridized to one another at a temperature or condition under which either of the two sequences would be capable of remaining hybridized to another molecular species. For example, a nucleic acid probe molecule that comprised the breakpoint sequence would be capable of stably hybridizing to the breakpoint region of the translocation since both the chromosome 8 and chromosome 21 portions of the probe and breakpoint could hybridize to one another. If, however, the nucleic acid molecule was less than 40 nucleotides in length, and preferably less than 30 nucleotides in length, the same probe would be substantially incapable of stably hybridizing to either chromosome 8 or chromosome 21.

Two sequence are said to be "complementary" to one another if they are capable of hybridizing to one another to form a stable anti-parallel double-stranded nucleic acid structure. Thus, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure.

Molecular characterization of the breakpoint regions of chromosomal translocations in human leukemic cells has enabled the identification of novel cellular protooncogenes and the elucidation of their mechanism of action (Solomon, E. et al., *Science* 254:1153–1160 (1991)). The genes found so far generally fit in the signal transduction cascade that control cellular growth and differentiation. While most of the oncogenes identified via retroviruses encode kinases, most of the genes identified via translocations are genes encoding nuclear proteins (Rabbitts, T. H., *Cell* 67:641–644 (1991); Cleary, M. L. *Cell* 66:619–622 (1991)). Indeed different genes for transcription factors with the basic helix-loop-helix domain, the homeo box domain and Zn finger motif have been shown to be susceptible to oncogenic conversion in leukemic cells (Cleary, M. L. *Cell* 66:619–622 (1991)).

AML M2 or M1 subtypes have recently been found to be characterized by a translocation between chromosome 8 and chromosome 21 (Miyoshi, H. et al., *Proc. Natl, Acad. Sci.* (U.S.A.) 88:10431–10434 (1991), herein incorporated by reference). Indeed, the translocation has been identified in approximately 18% of all AML cases of the M2 subtype (4th Int'l. Workshop on Chromosomes in Leukemia, *Cancer Genet. Cytogenet.* 11:284–287 (1948)). The gene that is rearranged due to the translocation has been designated AML1, and has been sequenced (Miyoshi, H. et al., *Proc. Natl. Acad. Sci.* (U.S.A.) 88:10431–10434 (1991)).

Recently the breakpoint region on chromosome 21 of the t(8;21)(q22; q22), a non-random cytogenetic defect of acute myelogenous leukemia with undifferentiated phenotype (see, Sandberg, A., In: *The Chromosomes in Human Cancer and Leukemia*, Elsevier, N.Y. (1990) for review) has been identified by using positional cloning strategies. Chromosome 21-specific YAC clones have been isolated and shown to identify the translocation in t(8;21) blast cells (Gao, J. et al., *Proc. Natl. Acad, Sci.* (U.S.A.) 88:4882–4886 (1991); Kearney, L. et al., *Cancer Genet. Cytogenet.* 57:109–119 (1991)). Moreover a clone isolated by a NotI linking library specific for chromosome 21 was found to be capable of detecting molecular rearrangements in t(8;21) patients' DNA (Shimizu, K. et al., *Genes Chrom. Cancer* 5:163–167 (1991)). The AML1 gene displays sequence homology to the Drosophila runt segmentation gene (Dag, A. et al., *Nature* 356:484 (1992)). The breakpoints of different patients seem to cluster between two AML1 exons, exon 5 and 6.

Expression studies indicated that multiple AML1 transcripts are expressed in normal cells (Miyoshi, H. et al., *Proc. Natl. Acad. Sci.* (U.S.A.) 88:10431–10434 (1991)). However the same study left open the question as to whether the translocation caused the deregulation of AML1 transcription or production of fusion transcripts between AML1 and transcribed sequences of a chromosome 8 gene.

Although the above studies disclose the sequence of the AML1 gene, they do not describe the sequence of the t(8;21) breakpoint. The present invention derives, in part, from the identification of gene sequences that flank the breakpoint of the t(8;21) translocation. Thus, the present invention permits the use of nucleic acid amplification strategies to amplify the translocation breakpoint, and hence provides a non-karyotypic method for diagnosing AML M2 or M1 subtype.

In order to identify the sequences that flank the translocation breakpoint, it is preferable to obtain and characterize the fusion transcripts from t(8;21) leukemic cells. Since such transcripts are present at low concentration, it is desirable to amplify them using a nucleic acid amplification procedure. Because the orientation of transcription relative to the breakpoint was unknown, it was possible that the transcript might originate in either the chromosome 8 or the chromosome 21 portion of the translocation. Thus, to both identify the breakpoint flanking sequences, and to define the orientation of transcription, Rapid Amplification of cDNA End (RACE) technology is preferably exploited to amplify sequences 3' or 5' to the AML1 gene (Frohman, M. A. et al., *Proc. Natl. Acad, Sci.* (U.S.A.) 85:8998–9002 (1988); Ohara, O. et al., *Proc. Natl. Acad. Sci.* (U.S.A.) 86.:5673–5677 (1989)). These procedures are also known as "one-sided PCR" or "anchored-PCR," and facilitate the recovery of full-length cDNAs from rare transcripts.

The 3' RACE procedure results in the amplification (using PCR, for example) of sequences 3' of a particular sequence known to be present in a desired molecule. To use the 3' RACE method to amplify sequences 3' to an AML1-specific primer, a poly dU-containing adapter primer is permitted to hybridize to the poly A tail of mRNA. The dU-containing primer contains a unique 5' portion, such that, upon extension using a reverse transcriptase, a cDNA complement to the mRNA is formed that possesses a unique sequence 5' to the poly dU region. After the formation of this molecule, the mRNA is removed (using heat, or more preferably, RNAse H, which degrades the RNA of RNA-DNA heteroduplexes). cDNA corresponding to the desired AML1 breakpoint fusion transcript can then be amplified using a pair of primers one of which is specific to the AML1 gene, and the other of which is specific to the unique sequence that was installed at the 5' end of the dU-containing primer.

5' RACE is preferably employed to amplify sequences located 5' to a particular AML1 primer sequence. Thus, an AML1-specific primer is permitted to hybridize to mRNA, and is then extended through the action of a reverse transcriptase. As in the case of 3' RACE, the mRNA is then removed from the cDNA extension product. The 3' terminus od the extension product is then extended through the action of deoxynucleotidyl transferase and a nucleotide such as dATP such that a 3' poly A terminus is created. The extended molecule is then permitted to hybridize to a dU-containing primer that has a unique 5' terminal sequence. The extension of this primer results in the production of a cDNA copy of the mRNA that contains the unique 5' terminal sequence. The extension product can then be amplified using primers that are capable of hybridizing to the unique sequence and to the AML1-specific sequence.

Most preferably, amplification of RACE products will be accomplished through the use of the "polymerase chain reaction" ("PCR") which achieves the amplification of a specific nucleic acid sequence using two oligonucleotide primers complementary to regions of the sequence to be amplified (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al,., U.S. Pat. No. 4,683,202; Erlich, H., U.S. Pat. No. 4,582,788; and Saiki, R. et al,, U.S. Pat. No. 4,683,194), which references are incorporated herein by reference). PCR is theoretically capable of mediating the exponential amplification of specific nucleic acid sequences. The method can be used to amplify either single or double stranded DNA. Reviews of the polymerase chain reaction are provided by Mullis, K. B. (*Cold Spring Harbor Symp. Quant. Biol.* 51:263–273 (1986)); Saiki, R.K., et al. (*Bio/Tecnology* 3:1008–1012 (1985)); and Mullis, K.B., et al. (*Met. Enzymol.* 155:335–350 (1987), which references are incorporated herein by reference). The specificity of the amplification can be increased using "nested PCR." In this embodiment, amplification is mediated using the unique sequence primer and a second AML1-specific primer that hybridizes to a sequence within the initial amplified products.

Both normal and chimeric AML1 transcripts were identified when the above-described amplification procedures were conducted. Whereas only normal transcripts were isolated by 5' RACE, both normal and fusion transcripts were identified by 3' RACE.

The identification of fusion transcripts indicates that the t(8;21) translocation resulted in the generation of at least one chimeric gene that is transcriptionally active. This gene on the 8q- derivative represents the fusion between the 5' region of the AML1 gene with the 3' region of a gene on chromosome 8 that has a region of homology with the cyclin D2 gene (Xiong, Y. et al., *Genomics* 13:575–584 (1992)).

The elucidation of the sequences that flank the t(8;21) translocation provides the means for diagnosing AML. Any of a variety of methods may be used for this purpose.

In one embodiment, the t(8;21) translocation can be detected through the use of "probes," using, for example, in situ hybridization. As used herein, a "probe" is a detectably labelled nucleic acid molecule that is capable of hybridizing to a defined site of a target molecule. Any of the nucleotide sequences disclosed herein can be used as a probe; the general requirement for such use being merely that the nucleic acid molecule be sufficiently long (generally 10 or more nucleotides in length) that it possesses the capacity to form stable hybridization products with the target molecule.

In this embodiment of the invention, the presence of AML is diagnosed through the use of a probe(s) that is/are capable of hybridizing to the breakpoint site, or to the regions that flank this site.

Any suitable means of detection may be employed; thus, the label may be an enzyme label, a fluorescent label, a radioisotopic label, a chemiluminescent label, etc. Examples of suitable enzyme labels include alkaline phosphatase, acetylcholine esterase, alpha-glycerol phosphate dehydrogenase, alkaline phosphatase, asparaginase, β-galactosidase, catalase, delta-5-steroid isomerase, glucose oxidase, glucose-6-phosphate dehydrogenase, glucoamylase, glycoamylase, luciferase, malate dehydrogenase, peroxidase, ribonuclease, staphylococcal nuclease, triose phosphate isomerase, urease, and yeast-alcohol dehydrogenase. Examples of suitable fluorescent labels include a fluorescein label, an isothiocyanate label, a rhodamine label, a phycoerythrin label, a phycocyanin label, an allophycocyanin label, an o-phthaldehyde label, a fluorescamine label, etc. Examples of suitable chemiluminescent labels include a luminal label, an isoluminal label, an aromatic acridinium ester label, an imidazole label, an acridinium salt label, an oxalate ester label, a luciferin label, an aequorin label, etc.

In one sub-embodiment of this method, a single t(8;21) translocation-specific probe is employed. In a second sub-embodiment, two probes are employed, one specific for the AML1 sequence and one specific for the chromosome 8 sequence at the translocation. In this embodiment, the two probes may employ the same label, but will preferably employ different labels, such that the probe that is specific for the AML1 sequence can be distinguished from the probe that is specific for the chromosome 8 sequence.

In accordance with this aspect of the invention, chromosomes would be incubated with the probe(s), and the label then detected. The presence of leukemic cells would be indicated by the recognition of a hybridized product between the breakpoint specific probe and chromosome 21. Alternatively, in the above-described sub-embodiment that employs two probes, leukemic cells would be indicated by the recognition of a single chromosome that had hybridized to both the AML1-specific and the chromosome 8-specific probe.

The above-described method differs from conventional karyotypic analysis in being more rapid, less technically demanding, and in permitting a larger number of cells to be analyzed.

In a preferred assay for AML, "primers" are employed that are capable of specifically amplifying only those nucleic acid transcripts that comprise the t(8;21) translocation, and the presence of leukemic cells is diagnosed by the amplification of a chromosome 8 - chromosome 21 fusion transcript. As used herein, a "primer" is a nucleic acid molecule that is capable of hybridizing to a target nucleic acid molecule, and of being extended in a template-dependent manner by a DNA or RNA polymerase. Any of the nucleotide sequences disclosed herein can be used as a probe; the general requirement for such use being merely that the nucleic acid molecule be sufficiently long (generally 10 or more nucleotides in length) that it possesses the capacity to form stable hybridization products with the target molecule, and that it have a free (i.e. unblocked) 3' hydroxyl terminus.

In this aspect of the invention, DNA or RNA of a sample may be subjected to amplification using any amplification method capable of amplifying a t(8;21) translocation-specific sequence. Thus, in addition to PCR or RACE, known transcription-based nucleic acid amplification procedures may be used (Kwoh D. et al., *Proc. Natl. Acad. Sci.* (U.S.A.) 86:1173 (1989); Gingeras T. R. et al., PCT appl. WO 88/10315 (priority: U.S. patent applications Ser. Nos. 064, 141 and 202,978, both now abandoned); Davey, C. et al. (European Patent Application Publication no. 329,822); Miller, H. I. et al., PCT appl. WO 89/06700 (priority: U.S. patent application Ser. No. 146,462, filed Jan. 21, 1988, now abandoned); Schuster, D., U.S. patent application Ser. No. 715,603, now U.S. Pat. No. 5,169,766). Similarly, ligation dependent methods may be employed (Wu, D. Y. et al., *Genomics* 4:560 (1989)).

In a preferred embodiment, a sense oligonucleotide from AML1 exon 5:
SEQ ID NO:1 TGTCGGTCGAAGTGGAAGAGG and an antisense oligonucleotide:
SEQ. ID NO:2 AAACTGAAACTCAAAGCCTGAAATGA
from the chromosome 8 gene comprise the most preferred probes and primers of the present invention. The use of these sequences as primers results in the amplification of a 227 bp fragment in leukemic cells, but does not result in amplification of any product in normal cells.

In a preferred embodiment, the methods of the present invention may be modified to remove the primer or probe sequence (or the complement of either sequence) after amplification. This can be accomplished by employing probe or primer molecules that contain one or more exo-sample nucleotides An "exo-sample nucleotide", as used herein, refers to a nucleotide which is generally not found in a sequence of DNA. For most DNA samples, deoxyuridine is an example of an exo-sample nucleotide. Although the triphosphate form of deoxyuridine, dUTP, is present in living organisms as a metabolic intermediate, it is rarely incorporated into DNA. When dUTP is incorporated into DNA, the resulting deoxyuridine is promptly removed in vivo by normal processes, e.g. processes involving the enzyme uracil DNA glycosylase (UDG) (Kunkel, U.S. Pat. No. 4,873,192; Duncan, B. K., *The Enzymes XIV*:565–586 (1981), both references herein incorporated by reference in their entirety). Thus, deoxyuridine occurs rarely or never in natural DNA. It is recognized that some organisms may naturally incorporate deoxyuridine into DNA. For nucleic acid samples of those organisms, deoxyuridine would not be considered an exo-sample nucleotide. Examples of other exo-sample nucleotides include bromodeoxyuridine, 7-methylguanine, 5,6-dihyro-5,6dihydroxy-deoxythymidine, 3-methyldeoxadenosine, etc. (see, Duncan, B. K., *The Enzymes XIV*:565–586 (1981)). Other exo-sample nucleotides will be evident to those in the art. For example, RNA primers used for DNA amplifications can be readily destroyed by base or an appropriate ribonuclease (RNase). RNase H degrades RNA of RNA:DNA hybrids and numerous single-strandedRNases are known which are useful to digest single-stranded RNA after a denaturation step.

Such exo-sample nucleotides may, and preferably will, be of the same type (i.e. all dU); alternatively, several different types of exo-sample nucleotides may be employed in the molecule. The removal of the introduced molecule is accomplished by treating the sample with an enzyme capable of hydrolyzing nucleic acid molecules which contain the exo-sample nucleotide (for example, by incubating the sample in the presence of UDG to remove all dU-containing sequences). This method is applicable to any in vitro procedures which utilize enzymes to amplify specific nucleic acid sequences and especially to PCR.

The use of one embodiment of this method to remove potential contaminants from samples being subjected to PCR amplification is disclosed by Berninger in U.S. patent application Ser. No. 07/401,840 (filed Sep. 1, 1989), now abandoned by Hartley, J. L., U.S. patent application Ser. No. 07/360,120 (filed Jun. 1, 1989), now U.S. Pat. No. 5,035, 996, and by Longo, M. C. et al. (*Gene* 93:125–128 (1990)), all of which references are herein incorporated by reference in their entirety. These references disclose the use of either dU-containing oligonucleotides or dUTP in the PCR-directed amplification of a target sequence. The sample is treated with UDG prior to amplification in order to eliminate any dU-containing DNA (derived from other prior PCR reactions) which may have contaminated the sample. The methods thus eliminate contamination of starting materials with the end products of previous amplification processes, and thereby address a major problem of nucleic acid amplification techniques.

The present invention is particularly adapted to compositions of matter such as kits. In a preferred embodiment, such kits will be specially adapted to hold a first container that contains an AML1-specific probe or primer molecule, and a second container that holds a chromosome 8-specific probe or primer. The kit may optionally also contain instructional brochures, standard concentration (assay calibration) reagents, etc.

Having now generally described the invention, the same will be more readily understood through reference to the following examples which are provided by way of illustration, and are not intended to be limiting of the present invention, unless specified.

EXAMPLE 1

AMPLIFICATION OF THE AML1 TRANSLOCATION FUSION TRANSCRIPT USING RAPID AMPLIFICATION OF CDNA ENDS ("RACE")

RNA was extracted from normal white blood cells isolated on Ficoll-Hypaque, from blasts of patients with t(8;21), and from a cell line Kasumi-1 (Asou, H. et al., *Blood* 77.:2031–2036 (1991)), that had been shown to be positive for the t(8;21) by conventional techniques (Chomzynski, P. et al., *Anal. Biochem*, 162:156–159 (1987)).

The first-strand synthesis of cDNA for 3' RACE experiments was accomplished by using an oligo dT adapter primer:
SEQ ID NO:3 GCCCACGCGTCGAC-TACTTTTTTTTTTTTTTTTTT
and SuperScript II RT reverse transcriptase (BRL) according to the manufacturer's protocol. To amplify cDNAs 3' to AML1 exon 5, the 3' RACE system (BRL, Gaithersburg, Md.) and two rounds of amplification by polymerase chain reaction (PCR) were used. For the first amplification two oligonucleotides were used, an AML1 exon 5 sense primer:
SEQ ID NO:4 TGTCGGTCGAAGTGGAAGAGG and an antisense universal amplification primer:
SEQ ID NO:5 CUACUACUACUAGGCCACGCGTC-GACTAGTAC that contained dUMP residues which enabled the 3' RACE products to be cloned by a method utilizing uracil DNA glycosylase (UDG) (Nisson, P. E. et al., *PCR Methods and Applications* 1:120–123 (1991)), Rashtchian et al., U.S. Pat. No. 5,137,814.

For the second amplification, a nested AML1 exon 5 sense primer containing dUMP residues was used:
SEQ ID NO:6 CAUCAUCAUCAUTGGATGGGC-CCCGAGAAC To obtain transcripts 5' to AML1 exon 6, the 5' RACE system (BRL) was employed. The first-strand synthesis of cDNA for 5' RACE experiments was accomplished by using an exon 6 AML1 antisense primer:
SEQ ID NO:7 AGGCACGAGGGTTGGGCG and SuperScript II RT reverse transcriptase. The cDNA was tailed with dCTP and terminal transferase (TdT) and amplified using a sense anchor primer:
SEQ ID NO:8 CUACUACUACUAGGCCACGCGTC-GACTAGTACGGGIIGGGIIGGGIIG and a nested exon 6 AML1 antisense primer:
SEQ ID NO:9 CAUCAUCAUCAUAGCCGCTCG-GAAAAGGACAAG After amplification, 5' and 3' RACE products were cloned into plasmid pAMP1 by using the Clone Amp system (BRL). Insert size was determined on individual bacterial colonies. Colonies were lysed in 1x PCR buffer (50 mM KCl, 10 mM Tris, pH 8.4, 0.001% gelatin, 1.5 mM $MgCl_2$) and the DNA amplified by PCR using pAMP1 specific primers for the M13 region:
SEQ ID NO:10 GTAAAACGACGGCCAGT and T7 promoter region:
SEQ ID NO:11 TAATACGACTCACTATAGGG that flank the cloning site. PCR products were analyzed on a 2% agarose gel. Inserts ranging from 200 to 600 bp were selected for molecular characterization.

EXAMPLE 2

CHARACTERIZATION OF THE AMPLIFIED AML1 CDNA PRODUCTS

The sequence of the amplified cDNAs cloned in pAMP1 was determined using the dideoxy sequencing method (ds DNA Cycle Sequencing System, BRL) using the T7 primer described above. Sequence comparisons were made using DNA Star software. The homology search was performed at the National Center for Biotechnology Information (NCBI) using the BLAST network service (Althschul, S. F., et al., *J. Molec. Biol.* 215:403–410 (1990)).

To assess the chromosome localization of the cDNA products specific primers were designed on the basis of their DNA sequence and used for PCR amplification on genomic DNA from human x hamster somatic cell hybrids, human placenta and hamster cells. PCR amplification was also performed on the agarase-purified DNA (see, Kearney, L. et al., *Cancer Genet. Cytogenet.* 57:109–119 (1991)) of a chromosome 21 YAC (C4C10) spanning the t(8;21). RNA amplification was performed by PCR on first-strand cDNA obtained by reverse transcription of total RNA with Super-Script II reverse transcriptase and an oligo(dT) primer (BRL) and purified on a GlassMax cartridge (BRL). For all PCR amplification experiments, the reaction composition and the cycling conditions were identical, with the exception of the annealing temperatures. 50 µl reactions were composed of 200 µM dNTPs, 1X PCR buffer, 1 µM oligonucleotide primers and a double stranded DNA or first strand cDNA template. The reaction mixtures were preheated for 5 minutes at 94° C., and held at 80° C. for 1 minute before adding 2.5 to 5 units of Taq DNA polymerase (Cetus). The reactions were cycled 30 times as follows: 45 seconds at 94° C., 30 seconds at the appropriate annealing temperature, 1 minute at 72° C. This was followed by a 10 minute incubation at 72° C. to repair ragged ends.

AML1 cDNAs were labeled by random primer extension and hybridized to a panel of cosmids isolated from two chromosome 21 cosmid reference libraries (Nizetic, D. et al., *Proc. Natl. Acad. Sci. (U.S.A.)* 88:3233–3237 (1991)) screened with the C4C10 YAC. Cosmids were identified on membranes containing the arrayed libraries (kindly provided by the Imperial Cancer Research Fund, London; Lehrach, H. et al., In: *Genome Analysis Volume 1: Genetic and Physical Mapping*, Davies, K. E. et al., eds., Cold Spring Harbor Laboratory Press, Cold Spring Harbor, pp. 39–81, (1990)) obtained by using as a probe the C4C10 YAC DNA suppressed with human Cot-1 DNA (BRL). Complete suppression of repeated sequences in the YAC was obtained by mixing 50 ng of $^{32}p$ labeled YAC DNA with 10 µg pYAC4 vector DNA and 100 µg of human Cot-1 DNA boiling the mixture, and incubating it at 65° C. for 2 hours.

EXAMPLE 3

CORRELATION BETWEEN THE TRANSLOCATION AND AML TRANSCRIPTION

5' and 3' RACE experiments were performed on total RNA from normal lymphocytes, from the Kasumi-1 cells and from leukemic blasts with the t(8;21) of two patients. Since it is known that the AML1 gene is located on chromosome 21 with the 5' region telomeric and that the breakpoint of the t(8;21) occurs within the AML1 gene between exons 5 and 6 (FIG. 1) the rationale for the RACE experiments was to use exons 5 and 6 primers for AML1 exon 5 and 6 to isolate fusion transcripts derived from AML1 and a gene on chromosome 8. AML1 exon 5 primers were designed to extend 3' to this exon to identify both normal AML1 transcripts and chimeric transcripts, if any, deriving from a putative transcriptionally active gene on the derivative chromosome 8q-. AML1 exon 6 primers were used to extend 5' to this exon and were expected to identify normal AML1 transcripts and chimeric transcripts, if any, deriving from a putative transcriptionally active gene on the derivative chromosome 21q+.

Figure 2:
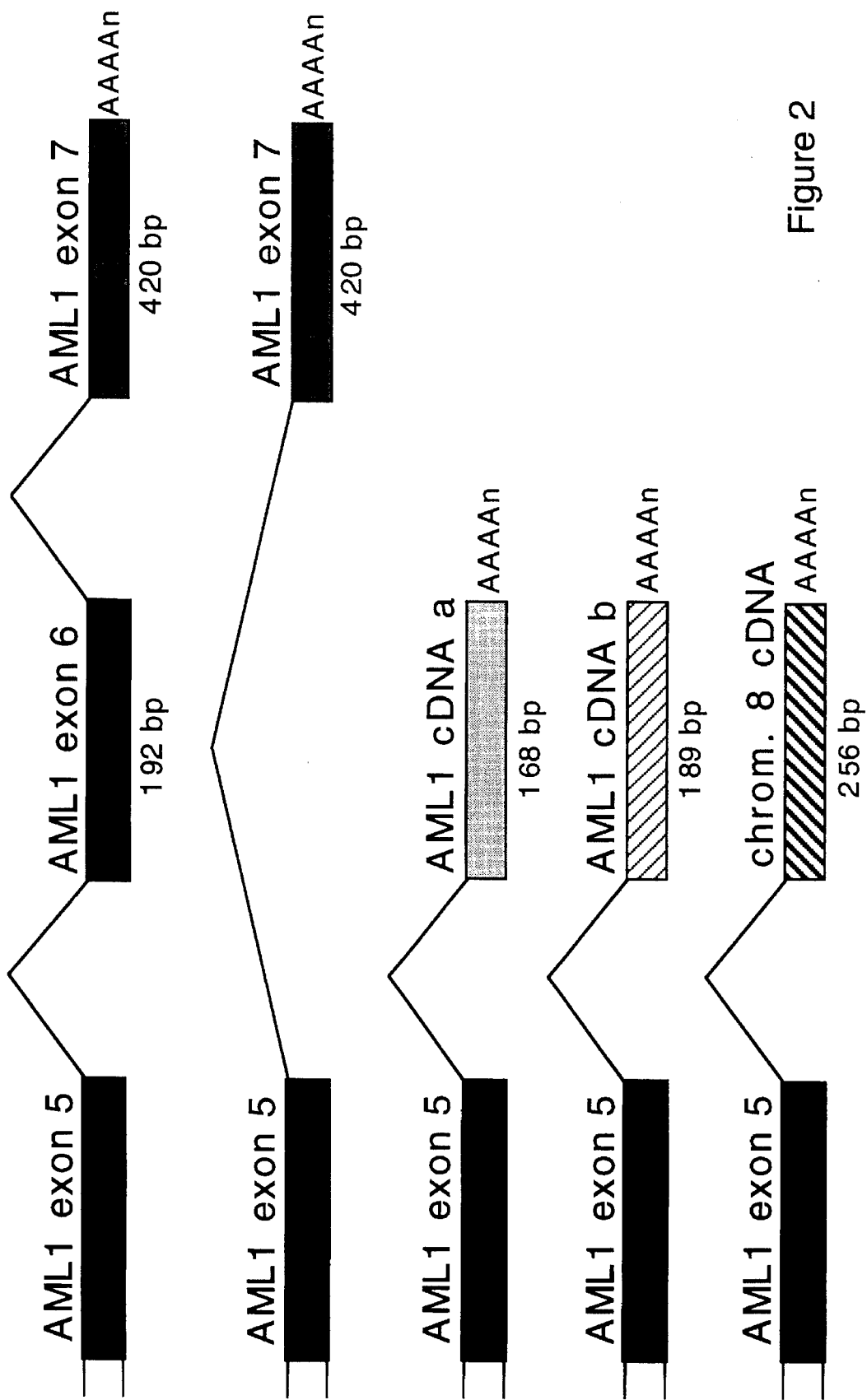
FIG. 2 shows a schematic representation of AML1 cDNAs isolated by 3' RACE. In t(8;21) RNA, both normal AML1 transcripts and a fusion transcript between AML1 and a novel chromosome 8 gene have been identified. Exon 5 has been observed to be spliced onto exons 6 and 7 as well as onto two novel AML1 cDNAs a and b. In addition, exon 5 has been found spliced onto a 256 bp cDNA that represents the 3' region of a gene on chromosome 8.

Sequence analysis of the amplified products obtained in the 3' RACE experiments identified both normal AML1 transcripts as well as a transcript derived from the fusion of AML1 with novel chromosome 8 sequences. Among the normal AML1 transcripts we identified four different transcripts in both normal lymphocytes and t(8;21) cells. Exon 5 was seen spliced on AML1 exon 6 as described previously by (Miyoshi, H. et al., Proc. Natl. Acad. Sci. (U.S.A.) 88:10431–10434 (1991)) as well as onto AML1 exon 7 (FIG. 2). In addition exon 5 was found spliced onto two novel sequences (FIG. 2), here referred as AML1 cDNA a and cDNA b, 168 and 189 bp long, respectively. Specific primers were designed for these two sequences.

PCR experiments using these primers and genomic DNA of somatic cell hybrids containing human chromosome 21 clearly showed that they are chromosome 21 specific. In the experiment, primers for cDNA a:
SEQ ID NO:12 CACTTNGNGCTGGTACACCCTCC
SEQ ID NO:13 AACTTTTTGGCTTTACGGGGG and primers for cDNA b:
SEQ ID NO:14 TCTTTGACCTGGCCTCGGTATCC were used on genomic DNA from human placenta, a monochromosome 21 somatic cell hybrid (153E7b), and the C4C10 YAC DNA. PCR products of either 130 bp (cDNA a) or 158 bp (cDNA b) were generated from all three DNAs. The PCR amplification was carried out as described above, but employing an annealing temperature for the cDNA a and b primers of 56° C. and 52° C. respectively.

Human-specific amplified products of 130 and 158 bp were also observed in the DNA of the C4C10 YAC on chromosome 21, that spans the t(8;21). The YAC contains the 3' region of the AML1 gene, including exon 5, 6 and 7. These results indicate that these two novel sequences are part of the 3' region of the AML1 gene.

Hybridization of these sequences to a panel of chromosome 21 cosmids isolated using the C4C10 YAC as probe did not identify any of the cosmids containing AML1 exon 7 (Table 1), indicating that these cDNA sequences must lie more 3' to this exon. The size of the PCR fragments amplified in the genomic DNA is the same as the one in the cDNAs. This indicated that the cDNA regions analyzed were not interrupted by introns. Comparison of the two cDNA sequences showed that they are different from each other. Table 1 provides a summary of DNA hybridization and PCR amplification experiments on a panel of cosmids identified by the C4C10 YAC probe showing that cDNA a and b must be 3' to AML1 exon 7, since they are not part of cosmids containing this exon; the 3' region of AML1 where the two sequences are located does not encompass the D21S65 locus identified by the sequences 525-3P 1A and 525-3P 1B (Kearney, L. et al., Cancer Genet. Cytogenet. 57:109–119 (1991)).

TABLE 1

| COSMIDS | C4C10 | EX 5 | EX 6 | EX 7 | cDNAa | cDNAb | 525-3P 1A | 525-3P 1B |
|---|---|---|---|---|---|---|---|---|
| ICRFc102HO9110 | + | − | − | − | − | − | + | + |
| ICRFc102EO952 | + | − | − | − | − | − | + | − |
| ICRFc102HO8116 | + | + | + | + | − | − | − | − |
| ICRFc102A03101 | + | − | − | − | − | − | − | + |
| ICRFc102F0137 | + | − | − | − | − | − | + | − |
| ICRFc102F1247 | + | − | − | − | − | − | + | − |
| ICRFc102F09103 | + | + | + | + | − | − | − | − |
| ICRFc103F0785 | + | + | − | − | − | − | − | − |
| ICRFc103C0664 | + | − | − | + | − | − | − | − |

In addition to normal AML1 transcripts in the RNA of t(8;21) leukemic blasts of one patient (PX 1) one transcript was identified representing splicing of AML1 exon 5 to a novel 256 bp sequence (FIG. 3; SEQ ID NO:17; SEQ ID NO:18).

The fact that this sequence was derived from chromosome 8 was determined through the use of PCR amplification using primers designed from this sequence:
SEQ ID NO:15 CACTCCACAATGCCAGACTCACC
SEQ ID NO:2 AAACTGAAACTCAAAGCCTGAAATGA
When these primers were used on genomic DNA from human placenta, a monochromosome 8 somatic cell hybrid (CH8), monochromosome 21 somatic cell hybrid (153E7b) and Chinese hamster (CHO-K1) a human specific product of 159 bp was observed in the somatic cell hybrid containing chromosome 8, but not in the monochromosomal 21 hybrid. The PCR conditions used as described above, however, an annealing temperature of 53° C. was employed. This result clearly indicated that the cDNA sequence isolated mapped to chromosome 8 and that this sequence was identical to the genomic sequence. This sequence contains a stretch of nucleotides highly homologous to a portion of the exon 2 region of a human D-type cyclin gene (FIG. 3).

EXAMPLE 4

CHARACTERIZATION OF THE AML GENE FUSION

To determine whether the chromosome 8 sequence might belong to a transcriptionally active gene fused to the AML1 gene in other leukemic blasts containing the t(8;21), PCR amplification was performed using a sense oligonucleotide from AML1 exon 5:
SEQ ID NO:1 TGTCGGTCGAAGTGGAAGAGG and an antisense oligonucleotide:
SEQ ID NO:2 AAACTGAAACTCAAAGCCTGAAATGA from the chromosome 8 gene and the first-strand cDNA of t(8;21) leukemic cells, PX 2 and PX 3, of Kasumi-1 cells and normal lymphocytes. This experiment revealed that the same 227 bp fragment amplified in PX 1 was also amplified in the cDNAs of the patients and in the cell line, but not in the cDNA of normal lymphocytes. The 227 bp product represents the junction region between AML1 exon 5 and the chromosome 8 gene when using the AML1 sense and antisense primers (SEQ ID NO:1 and SEQ ID NO:2) on first strand cDNA of PX 1. The same product was amplified from PX 2 and PX 3, from the Kasumi-1 line containing the t(8;21). The same product could not be amplified from normal lymphocytes. When the PCR products were transferred to nylon membranes and hybridized to the end-labelled oligonucleotides, both probes hybridized to the 227 bp fragment. These findings show that this AML1 fusion transcript is generated as result of the (8;21) translocation in leukemic cells.

It is noteworthy to mention that the RNA of the t(8;21) PX 3 was extracted from bone marrow cells at the remission stage of the disease. Nevertheless the presence of the 227 bp product clearly indicated that a residual minimal amount of t(8;21) malignant cells were still present in the bone marrow analyzed. Thus, these cells went undetected by cytogenetic analysis. this finding underscores the fact that the methods of the present invention are not only more rapid than prior art techniques, but are also more sensitive.

The 5' amplification of the AML1 cDNA from exon 6 was used to isolate AML1 transcripts from a putative chimeric gene on the derivative 21q+ chromosome. Sequence analysis of the 5' RACE products isolated showed only normal fusion between AML1 exon 6 onto exon 5. This result was obtained in both PX1 and PX2. In 5' and 3' RACE experiments, ten cDNA products were sequenced in each case. Therefore it is possible that no transcriptionally active gene is generated from the translocation of the 5' region of the chromosome 8 gene onto the 3' AML1 region. Alternatively the transcripts from this gene may be less abundant in comparison to normal transcripts in t(8;21) leukemic cells.

Thus, the above experiments succeeded in identifying a fusion transcript in the RNA of 8;21 leukemic cells that was expressed from a chimeric gene on the derivative chromosome 8q-. The chimeric gene was generated by the fusion of the 5' region of the AML1 gene and the 3' region of a gene that presents a region of homology with the second exon of the human cyclin D2 gene (Xiong, Y. et al., *Genomics* 13:575–584 (1992)).

AML1 was found to contain a limited stretch of homology with the Drosophila segmentation gene, runt, encoding a nuclear regulatory protein (Dag, A. et al., *Nature* 356:484 (1992)). Northern blot analysis in human cells showed that AML1 was expressed as multiple transcripts (Miyoshi, H. et al., *Proc. Natl. Acad, Sci.* (U.S.A.) 88.:10431–10434 (1991)) which, in view of the results described herein, suggest the occurrence of one or more mechanisms that generate eukaryotic transcripts' diversity: alternative initiation, splicing and polyadenylation. Indeed the above-described data indicate that alternative splicing occurs in the region of the gene 3' to exon 5, since it was possible to isolate by 3' RACE four cDNAs showing alternative splicing of exon 5 onto exon 6, exon 7 and onto two novel cDNA sequences (cDNA a and b). These two sequences may be exons of the AML1 gene.

The AML1 fusion transcript that was identified in 8;21 leukemic cells could be detected in all the 8;21 samples that were analyzed, including two additional patients and the Kasumi-1 cell line. This result clearly indicated that the observed transcript was consistently expressed in the cells positive for the translocation.

The 3' portion of the transcript, derived from a novel gene on chromosome 8, displayed some degree of homology with the cyclin D2 gene (Xiong, Y. et al., *Genomics* 13.:575–584 (1992)). D-type cyclins (Xiong, Y. et al., *Cell* 65:691–699 (1991)) like the more studied A- and B-type cyclins were first identified in Saccnaromyces cerevisiae and are expressed in all eukaryotic cells. Cyclins are regulatory subunits that act in conjunction with the protein serine kinase cdc2 to control the major decision points of the mitotic cell cycle (Hunter, T. et al., *Cell* 66:1071–1074 (1991)). There is mounting evidence that they are involved in oncogenesis (Hunter, T. et al., *Cell* 66:1071–1074 (1991)). This is true not only for cyclin A (Wang, J. et al., *Nature* 343:555–557 (1990); Giordano, A. et al., *Cell* 58 981–990 (1989); Pines, J. et al. *Nature* 346:760–763 (1990)) but also for cyclins of the D class that normally have a role in the G1 phase of the cell cycle. For example the PRAD1 gene rearranged in parathyroid tumors (Motokura, T. et al., *Nature* 350:512–515 (1991)) and identified as the BCL1 oncogene (Motokura, T. et al., *Nature* 350:512–515 (1991); Withers, D. A. et al., *Molec. Cell. Biol.* 11:4846–4853 (1991)) rearranged in B cell leukemias and in human breast cancers corresponds to the cyclin D1 gene (Xiong, Y. et al., *Cell* 65:691–699 (1991)). Recently human cyclin D2 and D3 genes have been isolated and shown to share the cyclin box region (Xiong, Y. et al., *Genomics* 13:575–584 (1992)).

Significantly, the chromosome 8 sequence identified in the fusion transcript contained a region that corresponds to one of the three highly conserved coding regions of mammalian D-type cyclins (Xiong, Y. et al., *Genomics* 13:575–584 (1992)).

It is likely that the derangement of a gene for a nuclear protein (AML1) and a gene with cyclin D-related function may well perturb the normal physiology of a somatic cell.

The cloning of the breakpoint junction of the chromosome 8q- permits the possibility of detecting the 8;21 translocation at the molecular level, and thus provides a diagnostic use for the present invention. The present invention shows that by using primers from the genomic regions flanking the breakpoint it is possible to amplify a diagnostic 227 bp fragment in the cDNA of 8;21 positive cells, but not in cells lacking the translocation. This PCR-based method is more sensitive than conventional cytogenetic analysis to monitor minimal residual disease as shown for patient PX 3. Thus, the present invention provides a molecular tool to improve the diagnosis and management of the t(8;21) leukemia.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for screening for the presence of leukemic cells in a sample wherein said sample contains suspected leukemic cells or RNA obtained from said suspected leukemic cells, said method comprising the steps:

(A) isolating RNA from said sample (B) incubating RNA molecules of said sample in the presence of two different polynucleotide molecules, wherein said different polynucleotide molecules have the nucleotide sequence SEQ ID NO:1 and SEQ ID NO:2, under conditions sufficient to permit said plyynucleotide molecules to reverse transcribe a polynucleotide region of a target RNA molecule, if said target RNA molecule is present in said sample, and to then amplify said reverse transcribed polynucleotide region: wherein said target RNA molecule arises from transcription of a chromosomal t(8;21) junction of a translocation characteristic of a leukemic cell;

(C) determining whether said step (B) results in the amplification of a polynucleotide having said t(8;21) junction by detecting amplified polynucleotides having said t(8;21) junction, whereby the presence of said amplified polynucleotide is suggestive of the presence of leukemic cells or RNA from said cells.

2. The method of claim 1, wherein said amplification employs a polymerase chain reaction.

3. The method of claim 2, wherein said amplification employs a nested polymerase chain reaction using polynucleotides having the sequences SEQ ID NO:1 and SEQ ID NO:15 as primers.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:

(A) LENGTH: 21 base pairs
(B) TYPE: nucleic acid
(C) STRANDEDNESS: single
(D) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
(A) ORGANISM: HOMO SAPIENS ( v i i i ) POSITION IN GENOME:
(A) CHROMOSOME/SEGMENT: 21

( x i ) SEQUENCE DESCRIPTION: SEQ ID NO:1:

TGTCGGTCGA AGTGGAAGAG G     21

( 2 ) INFORMATION FOR SEQ ID NO:2:

( i ) SEQUENCE CHARACTERISTICS:
(A) LENGTH: 27 base pairs
(B) TYPE: nucleic acid
(C) STRANDEDNESS: single
(D) TOPOLOGY: linear ( i i ) MOLECULE TYPE: cDNA ( i i i ) HYPOTHETICAL: NO ( i v ) ANTI-SENSE: YES ( v i ) ORIGINAL SOURCE:
(A) ORGANISM: HOMO SAPIENS ( v i i i ) POSITION IN GENOME:
(A) CHROMOSOME/SEGMENT: 8

( x i ) SEQUENCE DESCRIPTION: SEQ ID NO:2:

AAACTGAAAC TCAAAAGCCT GAAATGA     27

( 2 ) INFORMATION FOR SEQ ID NO:3:

( i ) SEQUENCE CHARACTERISTICS:
(A) LENGTH: 34 base pairs
(B) TYPE: nucleic acid
(C) STRANDEDNESS: single
(D) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
(A) ORGANISM: HOMO SAPIENS ( v i i i ) POSITION IN GENOME:
(A) CHROMOSOME/SEGMENT: 21

( x i ) SEQUENCE DESCRIPTION: SEQ ID NO:3:

GCCCACGCGT CGACTACTTT TTTTTTTTT TTTT     34

( 2 ) INFORMATION FOR SEQ ID NO:4:

( i ) SEQUENCE CHARACTERISTICS:
(A) LENGTH: 21 base pairs
(B) TYPE: nucleic acid
(C) STRANDEDNESS: single
(D) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: HOMO SAPIENS ( v i i i ) POSITION IN GENOME:
    ( A ) CHROMOSOME/SEGMENT: 21

( x i ) SEQUENCE DESCRIPTION: SEQ ID NO:4:

TGTCGGTCGA AGTGGAAGAG G      21

( 2 ) INFORMATION FOR SEQ ID NO:5:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: YES ( i v ) ANTI-SENSE: YES ( v i ) ORIGINAL SOURCE:
    ( A ) ORGANISM: HOMO SAPIENS ( v i i i ) POSITION IN GENOME:
    ( A ) CHROMOSOME/SEGMENT: 21

( x i ) SEQUENCE DESCRIPTION: SEQ ID NO:5:

CUACUACUAC UAGGCCACGC GTCGACTAGT AC      32

( 2 ) INFORMATION FOR SEQ ID NO:6:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: HOMO SAPIENS ( v i i i ) POSITION IN GENOME:
    ( A ) CHROMOSOME/SEGMENT: 21

( x i ) SEQUENCE DESCRIPTION: SEQ ID NO:6:

CAUCAUCAUC AUTGGATGGG CCCCGAGAAC      30

( 2 ) INFORMATION FOR SEQ ID NO:7:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES (v i) ORIGINAL SOURCE:
    (A) ORGANISM: HOMO SAPIENS (v i i i) POSITION IN GENOME:
    (A) CHROMOSOME/SEGMENT: 21

(x i) SEQUENCE DESCRIPTION: SEQ ID NO:7:

AGGCACGAGG GTTGGGCG                                                                                         18

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: cDNA (i i i) HYPOTHETICAL: YES (i v) ANTI-SENSE: NO (v i) ORIGINAL SOURCE:
        (A) ORGANISM: HOMO SAPIENS (i x) FEATURE:
        (A) NAME/KEY: misc_feature
        (B) LOCATION: 36..47
        (D) OTHER INFORMATION: /note="W DENOTES INOSINE"

(x i) SEQUENCE DESCRIPTION: SEQ ID NO:8:

CUACUACUAC UAGGCCACGC GTCGACTAGT ACGGGWWGGG WWGGGWWG                                                        48

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: YES (v i) ORIGINAL SOURCE:
        (A) ORGANISM: HOMO SAPIENS (v i i i) POSITION IN GENOME:
        (A) CHROMOSOME/SEGMENT: 21

(x i) SEQUENCE DESCRIPTION: SEQ ID NO:9:

CAUCAUCAUC AUAGCCGCTC GGAAAAGGAC AAG                                                                        33

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: M13

( x i ) SEQUENCE DESCRIPTION: SEQ ID NO:10:

GTAAAACGAC GGCCAGT                                                                                              17

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: T7

( x i ) SEQUENCE DESCRIPTION: SEQ ID NO:11:

TAATACGACT CACTATAGGG                                                                                           20

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS ( v i i i ) POSITION IN GENOME:
        ( A ) CHROMOSOME/SEGMENT: 21

( x i ) SEQUENCE DESCRIPTION: SEQ ID NO:12:

CACTTNGNGC TGGTACACCC TCC                                                                                       23

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS ( v i i i ) POSITION IN GENOME:
        ( A ) CHROMOSOME/SEGMENT: 21

( x i ) SEQUENCE DESCRIPTION: SEQ ID NO:13:

AACTTTTTGG CTTTACGGGG G                                                                                         21

( 2 ) INFORMATION FOR SEQ ID NO:14:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: HOMO SAPIENS ( v i i i ) POSITION IN GENOME:
    ( A ) CHROMOSOME/SEGMENT: 21

( x i ) SEQUENCE DESCRIPTION: SEQ ID NO:14:

TCTTTGACCT GGCCTCGGTA TCC    23

( 2 ) INFORMATION FOR SEQ ID NO:15:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: HOMO SAPIENS ( v i i i ) POSITION IN GENOME:
    ( A ) CHROMOSOME/SEGMENT: 8

( x i ) SEQUENCE DESCRIPTION: SEQ ID NO:15:

CACTCCACAA TGCCAGACTC ACC    23

( 2 ) INFORMATION FOR SEQ ID NO:16:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( v i ) ORIGINAL SOURCE:
    ( A ) ORGANISM: HOMO SAPIENS ( v i i i ) POSITION IN GENOME:
    ( A ) CHROMOSOME/SEGMENT: 8

( x i ) SEQUENCE DESCRIPTION: SEQ ID NO:16:

CTTGAGTAGT TGGGGGAGGT GG    22

( 2 ) INFORMATION FOR SEQ ID NO:17:

( i ) SEQUENCE CHARACTERISTICS:
    ( A ) LENGTH: 256 base pairs
    ( B ) TYPE: nucleic acid
    ( C ) STRANDEDNESS: single
    ( D ) TOPOLOGY: linear ( i i ) MOLECULE TYPE: cDNA

```
        ( i i i ) HYPOTHETICAL: NO ( i v ) ANTI-SENSE: NO ( v i ) ORIGINAL SOURCE:
                ( A ) ORGANISM: HOMO SAPIENS ( v i i i ) POSITION IN GENOME:
                ( A ) CHROMOSOME/SEGMENT: T(8;21)

( i x ) FEATURE:
                ( A ) NAME/KEY: misc_feature
                ( B ) LOCATION: 103..142
                ( D ) OTHER INFORMATION: /note="Region of homology to human
                      cyclin D2 region (SEQ ID NO: 18)"

( x i ) SEQUENCE DESCRIPTION: SEQ ID NO:17:

ATCGTACTGA   GAAGCACTCC   ACAATGCCAG   ACTCACCTGT   GGATGTGAAG   ACGCAATCTA         60

GGCTGACTCC   TCCAACAATG   CCACCTCCCC   CAACTACTCA   AGGAGCTCCA   AGAACCAGTT        120

CATTTACACC   GACAACGTGT   AAGTAGTCAT   TTCAGGCTTT   TGAGTTTCAG   TTTTAAAGTT        180

TAAATTAAAT   TTTTTTCTGC   AAATGAAAAA   TCAAGGGAAA   TAAAATTCAG   CATCAATGTA        240

TTATGCAGAA   TGAACC                                                               256

( 2 ) INFORMATION FOR SEQ ID NO:18:

( i ) SEQUENCE CHARACTERISTICS:
                ( A ) LENGTH: 34 base pairs
                ( B ) TYPE: nucleic acid
                ( C ) STRANDEDNESS: single
                ( D ) TOPOLOGY: linear .( i i ) MOLECULE TYPE: cDNA ( i i i ) HYPOTHETICAL: NO ( i v ) ANTI-SENSE: NO ( v i ) ORIGINAL SOURCE:
                ( A ) ORGANISM: HOMO SAPIENS ( v i i ) IMMEDIATE SOURCE:
                ( B ) CLONE: HUMAN CYCLIN D2 REGION ( x i ) SEQUENCE DESCRIPTION: SEQ ID NO:18:

GACCGCGGAG   AAGCTGTGCA   TTTACACCGA   CAAC                                        34
```